(12) United States Patent
Su et al.

(10) Patent No.: US 9,146,222 B2
(45) Date of Patent: Sep. 29, 2015

(54) SYSTEM FOR DETECTING VOLATILE ORGANIC COMPOUNDS AND THE METHOD FOR FORMING THE SAME AND UTILITY THEREOF

(71) Applicant: National Taiwan University, Taipei (TW)

(72) Inventors: Wei-Fang Su, New Taipei (TW);
Che-Pu Hsu, Yilan County (TW);
Chun-Fu Lu, Taipei (TW);
Hsueh-Chung Liao, Taoyuan County (TW); Ming-Chung Wu, Tainan (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 327 days.

(21) Appl. No.: 13/860,839

(22) Filed: Apr. 11, 2013

(65) Prior Publication Data
US 2014/0103231 A1    Apr. 17, 2014

(30) Foreign Application Priority Data
Oct. 11, 2012    (TW) .............................. 101137557 A

(51) Int. Cl.
*G01N 27/22*    (2006.01)
*G01N 33/00*    (2006.01)
(52) U.S. Cl.
CPC .................................. *G01N 33/0047* (2013.01)

(58) Field of Classification Search
CPC ........................... G01N 33/0047; G01N 27/22
USPC ................... 250/578.1; 324/679; 356/72, 437
See application file for complete search history.

(56) References Cited

U.S. PATENT DOCUMENTS

| | | | | |
|---|---|---|---|---|
| 5,478,452 A | * | 12/1995 | Chriswell et al. | 436/153 |
| 2004/0009605 A1 | * | 1/2004 | Brown et al. | 436/149 |
| 2014/0021967 A1 | * | 1/2014 | Kang et al. | 324/679 |

OTHER PUBLICATIONS

Hsu, et al, Polymer-Nanoparticle Hybrid Materials for Volatile Organic Compounds (VOCs) Sensor, Apr. 12, 2012, MRS Spring Meeting.

* cited by examiner

*Primary Examiner* — Seung C Sohn
(74) *Attorney, Agent, or Firm* — WPAT, PC; Justin King

(57) ABSTRACT

The system for detecting volatile organic compounds (VOCs) of this present invention comprises a detecting material made by blending a nano-material and a conductive polymer. The system for detecting VOCs presents the property of high sensitivity, high sensing accuracy, quick response, and real-time VOC detecting, and is demonstrated in the present work for commercialization usage. The system for detecting VOCs can be easily operated to detect VOC without electronic detecting method, and hence this invention can reduce a lot of operation energy and procedure. Furthermore, when adding inorganic nanoparticles, the area of VOC exposure of this invention is increased and the molecular morphology variation of the detecting material is enhanced, and hence the detecting activity of the system for detecting VOCs is improved.

29 Claims, 6 Drawing Sheets

SYSTEM FOR DETECTING VOLATILE ORGANIC COMPOUNDS AND THE METHOD FOR FORMING THE SAME AND UTILITY THEREOF

BACKGROUND OF THE INVENTION

1. Field of the Invention

The present invention relates to a detecting system, and more particularly, to a system for detecting VOCs, a method for forming the mentioned system, and the utility of the mentioned system.

2. Description of the Prior Art

Today, the majority of typical volatile organic compounds with toxic, explosive, flammable, and environmental hazards have been widely used in the manufacture of various industrial products, and all sorts of chemical experiments. In a variety of industrial products and its research, such as semiconductor, petrochemical, and chemical, volatile organic compounds (VOCs) are often used during production of those industrial products as reagents, solvents, additives, intermediate or final product. For example, VOCs can be used in the development of pharmaceutical, cleaning fluid, oil, and the like. In general, those volatile organic compounds are very dangerous to people and environment, because they are explosive, flammable, and toxic. If VOCs are leaked out, it may bring about serious calamity, such as explosion, fire accident, etc., cause people huge damage on health and wealth, and bring acute problem of environmental pollution. For example, on May 17, 2012, in one chemical plant in Changhua County, Taiwan, Changhua Coastal Industrial Park, there was a huge explosion because of accident during toluene stirring, and the explosion resulted in one death and 13 injuries. In another case, a refinery explosion in Texas city, U.S.A. due to the leakage of volatile organic compounds which caused over 100 people injured and 15 confirmed death. Therefore, it should be extremely careful on the storage tanks, the pipes, and any processing about volatile organic compounds. In addition, if exposed to volatile organic compounds, it is in a high proportion that people will have allergies as asthma, cancer, and other diseases. Therefore, in order to protect human health and the environment, be subject to the harm caused by the leakage of volatile organic compounds or vaporization thereof, it is an extremely important matter to timely and accurately monitor the storage and transport of volatile organic compounds. The detection of toxic compounds is not only to ensure the safety of human health and property, but also to avoid the occurrence of environmental disasters.

The study of detecting VOC began in 1982 by Dodd and Persaud et al. Dodd and Persaud et al demonstrated the concept of electronic noise, based on an electronic apparatus similar to the human nose. The electronic apparatus was able to identify the smell characteristics around different compounds by detecting resistivity, voltage, current, frequency rates of change, and the like. Some methodologies are recently applied to commercial available sensor products, for example, semiconductor sensing method, catalytic combustion method, electrochemical sensing method, infrared sensing method, etc. Most of these sensor products are extremely expensive, for instance, an infrared sensor for sensing the leakage of VOCs costs over 130,000 US dollars. Apparently, the popularization of these sensor products is limited by the expensive cost. Especially, to our best knowledge today, there is still no commercial VOC sensor that can be massively equipped anywhere including each joint between transporting pipes, each switch of storage tanks, or other all high risky regions that VOC may be leaked out.

The common VOCs detecting technology is as the following. One commonly detecting technology is resistive measurement. A resistive measurement is performed by detecting the concentration of known volatile organic compounds via the changes of resistance. But, the lifetime of the detective material of resistive measurement is about 1 year. Another detecting technology is performed by employing detective material as the target detecting substrate. The target detecting substrate can bond with specific detective target, and the variation of the spectrum, such as fluorescent spectrum or Raman spectrum, of the target detecting substrate molecular with the specific detective target is recorded to determine the types and the concentration of organic compounds. The mentioned target detecting substrate is expensive, and the mentioned measurement is complicate and with long time. Still another VOC detecting technology is employing IR (infrared) spectroscopy to determine the type and concentration of organic compounds directly. The IR spectroscopy measurement is not widely used in industry because of the expensive cost, difficult maintenance, sensitive to moisture, and complicate testing sample collection and preparation. Accordingly, the development of a volatile organic compound(s) detecting system is the major target for the current industry development.

SUMMARY OF THE INVENTION

In view of the above background and special requirements of the industry, the present invention provides a system for detecting volatile organic compounds (VOCs), which address the issues that are not yet solved in the prior art.

An objective of the present invention provides a system for detecting the type and concentration of VOCs present in air. The system for detecting VOCs is constructed of a displace-able/disposable detective member and an optical measuring module for detecting VOCs module. The optical measuring module for detecting VOCs module comprises two visible light sources respectively with single wavelength, a detecting device, a light intensity sensing device, a data analyzing device, and a displaying device. According to the design of this invention, the displace-able/disposable detective member is exposed to th VOCs, and the absorption of the mentioned detective member is different while using different wavelength. The detected VOCs can be determined by the ratio of absorbance of different wavelength. The sensitivity of the detective member is from the morphology variation of a conductive polymer when the conductive polymer contacting with the VOCs. During forming the detective member from the conductive polymer by spin coating process, there is no sufficient time for the conductive polymer to accomplish organized morphology. And, additional nanoparticles can be dispersed into the molecular structure of the conductive polymer to keep the conductive polymer away from the formation of molecular arrangement morphology by $\pi$-$\pi$ stacking. When the membrane contacting with VOCs, the VOCs molecule is going to enter the molecular structure of the conductive polymer and make the nanoparticles moving away from the polymeric chain of the conductive polymer. The molecular morphology of the conductive polymer will be rearranged by the enhanced $\pi$-$\pi$ stacking effect among the conductive polymer, and the number of the ordered packing of the conductive polymer is increased for organized morphology. Because of the variation of molecular arrangement of the conductive polymer, the optical property of the detective member is changed, and the detective member can be used to detect the VOCs.

The present invention provides a system for detecting VOCs constructed of a displace-able/disposable detective member and an optical measuring module for detecting VOCs module. The detective member comprises a detective material. The existence and concentration of VOCs can be detected through the variation of the optical property of the detective material upon exposure to the VOCs. In this invention, the VOCs detection is achieved by the optical variation of the detective material on the detective member. The detective material is a composite material comprises polymer and nanoparticle. The optical property of the composite material can be changed by varying the morphology of the composite material when contacting with the VOCs. The detective member can be produced by low-cost traditional film-coating process, such as spin coating, spray coating, and dip coating. Through the calibrating and calculating by the build-in software of the system for detecting VOCs, the specie(s) and the concentration of the detected VOCs can be displayed. Besides, because the detecting member is disposable, the system for detecting VOCs will not easily be damaged or polluted by the VOCs. Moreover, the reliability of the system for detecting VOCs can be effectively improved, and the lifetime of the system for detecting VOCs can be validly extended. The mentioned system for detecting VOCs can be placed at the pipeline junction or the tank of the VOCs for instantly monitoring whether the VOCs is leaked or whether the VOCs concentration in air is too high. The mentioned system for detecting VOCs also can be placed in cars, elevators, cabins, factories, laboratories, or any other space with the necessary of monitoring possible VOCs presence and leakage.

The present invention provides a system for detecting VOCs constructed of a disposable detective member and an optical measuring module for detecting VOCs module with visible light source. Because the advantages of the simply manufacturing for producing detective member, the convenient operating, the low cost, the less limitation of environment, the competitive ability of the mentioned system for detecting VOCs is stronger than the commonly resistive measurement. The mentioned system for detecting VOCs also presents the advantage of high sensitivity, high selectivity, and low power consumption. Additionally, comparing with another VOCs detecting technology, IR spectrometer, an user can directly and easily operates the mentioned system for detecting VOCs of this invention to obtain the relative information of the detected VOCs without any IR spectrum knowledge.

Another objective of this present invention provides a disposable detective member. The detective member comprises a transparent substrate and a detective material. The detective member can be formed by coating the detective material with low temperature solution manufacturing process, such as spin coating, spray coating, or dip coating. The detective member can be manufactured under room temperature. The major component of the mentioned detective material is polymeric composite material. The detective material comprises anti-$\pi$-$\pi$ stacking compound in nanoscale and conductive polymer with $\pi$-$\pi$ stacking effect molecular structure. The mentioned detective member is disposable, easily operated, and low-cost.

The recently VOCs detecting apparatus generally are expensive and not widely used. In order to overcome the shortcomings of the VOCs detecting apparatus in the prior art, this present invention provides a system for detecting VOCs with the advantage of low cost, conveniently operating, and high selectivity, etc., so that the mentioned system for detecting VOCs can be used to replace the traditional VOCs detecting apparatus. And, the system for detecting VOCs of this present invention can achieve the functionality of the on-site monitoring. That is, the mentioned system for detecting VOCs is a convenient and practical security guarding device for oil companies, factories, laboratories, and families on real-time monitoring whether the VOCs leaked and the leaked concentration of VOCs.

According to the above objectives, this present invention provides a detective material for detecting VOCs. The detective material comprises a conductive polymer with the $\pi$-$\pi$ stacking effect molecular structure, and an anti-$\pi$-$\pi$ stacking compound in nanoscale. The anti-$\pi$-$\pi$ stacking compound is dispersed in the molecular structure of the conductive polymer to keep the morphology of the molecular structure of the conductive polymer away from being changed by $\pi$-$\pi$ stacking effect. The anti-$\pi$-$\pi$ stacking compound will aggregate and move away from the molecular structure of the conductive polymer when the anti-$\pi$-$\pi$ stacking compound contacting with VOC, and the morphology of the molecular structure of the conductive polymer will rapidly changed by $\pi$-$\pi$ stacking effect when the anti-$\pi$-$\pi$ stacking compound moving away from the molecular structure of the conductive polymer. The conductive polymer is selected from one of the following, the derivatives thereof, or any combinations thereof: poly(3-hexylthiophene) (P3HT), poly(p-phenylene vinylene), polyfluorene, poly(thieno[3,4-b]-thiophene-alt-benzodithiophene), poly(thiophene-alt-isoindigo), poly(cyclopentadithiophene-alt-isoindigo), poly(diketopyrrolopyrrole-alt-4,5-diaza-9,9'-spirobifluorene), {poly(cyclopentadithiophene-alt-benzothiadiazole)}, poly[2,6-(4,4-bis(2-ethylhexyl)-4H-cyclopenta[2,1-b;3,4-b'] dithiophene)-alt-4,7(2,1,3-benzothizdiazle)] (PCPDTBT), and poly(benzodithiophene-thiophene-cyanovinylene) (PCBN). The anti-$\pi$-$\pi$ stacking compound is selected from one of the following, or any combinations thereof: inorganic nanomaterials, fullerene derivatives. The fullerene derivatives is selected from one of the following, the derivatives thereof, or any combinations thereof: (6,6)-phenyl-$C_{61}$ butyric acid methyl ester ($PC_{61}BM$), (6,6)-phenyl-$C_{71}$ butyric acid methyl ester ($PC_{71}BM$).

According to the above objectives, this present invention provides a method for forming a device for detecting VOCs. The mentioned method for forming a device for detecting VOCs comprises performing a first blending process to blend a conductive polymer with an anti-$\pi$-$\pi$ stacking compound in a solution to form a first blended material, wherein the conductive polymer is with the $\pi$-$\pi$ stacking effect molecular structure, wherein the anti-$\pi$-$\pi$ stacking compound is in nanoscale; performing a standing process to disperse the anti-$\pi$-$\pi$ stacking compound into the molecular structure of the conductive polymer to prevent $\pi$-$\pi$ stacking effect occurred in the conductive polymer; and performing a coating process to form a detecting layer with the first blended material onto a surface of a transparent substrate. The mentioned solution can be chloroform. After performing the standing process, the mentioned method for forming a device for detecting VOCs can optionally performing a second blending process to add an inorganic nanomaterial into the first blended material to form a second blended material, and the detecting layer is formed with the second blended material in the following coating process. The inorganic nanomaterial is added for increasing the surface area of detective member of the device for detecting VOCs.

According to the above objectives, this present invention provides a system for detecting VOCs. The mentioned system for detecting VOCs comprises a light providing module for providing full-spectrum light source; a detecting module located at a first specific location in one optical path of the light providing module to receive the light from the light providing module; an accommodating space between the light providing module and the detecting module, wherein the accommodating space is employed for introducing and storing the VOC; a light sensing module located at a second specific location in the same optical path of the light providing module to detect the light variation of the light from the light providing module and across the detecting module, wherein the light sensing module will generate a electric signal based on the light variation; and an analyzing and controlling module communicating with the light sensing module and receiving the electric signal from the light sensing module, wherein the analyzing and controlling module can analyze the electric signal to identify whether there is VOCs in-situ. The light providing module comprises a laser light source, or a light emitting diode (LED) light source. The light providing module comprises a first light source and a second light source, when the detecting module exposed to the environment with VOCs, the light absorption peak of the first light source is unaffected and being as the control standard value, and the light absorption peak of said second light source is variated with the change the detecting material of the detecting module so that the light absorption peak of the second light source is as the detective variation value. The selection of the first light source and the second light source is from one of the following wavelength pair: the wavelength of the first light source at about 510 nm to 520 nm and the wavelength of the second light source at about 550 nm to 610 nm, the wavelength of the first light source at about 545 nm to 585 nm and the wavelength of the second light source at about 630 nm to 650 nm, the wavelength of the first light source at about 690 nm to 700 nm and the wavelength of the second light source at about 745 nm to 755 nm.

The mentioned detecting module comprises a detecting layer being opposite to the light irradiating direction of the light providing module for receiving the light from the light providing module. The thickness range of the detecting layer is about 10 nanometer to 10 micrometer. The detectable limitation of the VOCs concentration is depended on controlling the thickness of the detecting layer of the system for detecting VOCs. The detecting layer comprises a conductive polymer, and an anti-π-π stacking compound, wherein the anti-π-π stacking compound is in nanoscale, wherein the conductive polymer is with the molecular structure of π-π stacking effect. The anti-π-π stacking compound is dispersed into the molecular structure of the conductive polymer to prevent π-π stacking effect occurred in the conductive polymer. The anti-π-π stacking compound will aggregate and move away from the molecular structure of the conductive polymer when the anti-π-π stacking compound contacting with VOC. The morphology of the molecular structure of the conductive polymer will rapidly changed by π-π stacking effect when the anti-π-π stacking compound moving away from the molecular structure of the conductive polymer. The conducting layer is formed by one of the following way: blending the conductive polymer with fullerene derivatives, blending the conductive polymer with inorganic nanoparticles, and blending the conductive polymer with fullerene derivatives and inorganic nanoparticles.

The mentioned light sensing module comprises a light intensity detecting device, wherein the light sensing module can perform photo-electric conversion by the light intensity detecting device, wherein the light intensity detecting device can receive the light from the light providing module and across the detecting module, and convert the received light into the electric signal. The analyzing and controlling module can further comprise an analyzing unit comprising a default database and a default detecting area, wherein the analyzing unit can analyze and calculate the electric signal to obtain the sensitivity S, wherein the sensitivity S is compared with the data in the default database; and a controlling unit, wherein when the sensitivity S is matched with a value range of VOC in the default database, the analyzing and controlling module will drive the controlling unit to generate a controlling signal. The analyzing and controlling module can further comprise a displaying unit communicating with the controlling unit, wherein the displaying unit can receive the controlling signal from the controlling unit and display the information of the specie(s) of the detected VOC(s), the concentration of the detected VOC(s), and the area where the VOC(s) is detected. The default database can provide the sensitivity S corresponding to the specific VOCs, wherein the sensitivity S can be determined as $S_a$ and $S_v$ with the voltage difference $\Delta V$ or absorbance A:

$$S_a = [(A_x/A_y)_a/(A_x/A_y)_b] - 1,$$

$$S_v = [(\Delta V_x/\Delta V_y)_a/(\Delta V_x/\Delta V_y)_b] - 1,$$

wherein x is represented the wavelength of the second light source, y is represented the wavelength of the first light source, a is represented the condition before exposed to VOCs, and b is represented the condition after exposed to VOCs.

The mentioned system for detecting VOCs can further comprise an alarming module, wherein the alarming module can receive the controlling signal and generate a warning, wherein the alarming module comprises a warning light device, a warning sound device, and a warning communicating device, wherein the warning communicating device can notify the emergency disposal units or the rescue units where the VOC(s) is, what specie(s) the VOC(s) is, and what concentration the VOC(s) is through wire or wireless communication.

According to the above objectives, this present invention provides a method for detecting VOCs. The mentioned method for detecting VOC comprises the following steps: performing a gas-introducing process for introducing the VOCs into an accommodating space, wherein the accommodating space comprises a light providing module and a detecting module, wherein the detecting module is located at a specific location in an optical path of the light providing module to receive the light from the light providing module; performing a detecting process by the detecting module, wherein the detecting module is adequately contacted with the VOCs; performing a light sensing process by a light sensing module, wherein the light sensing module can perform photo-electric conversion, wherein the light sensing module can generate an electric signal corresponding to the absorbance variation in the detecting module; and performing an analyzing and controlling process by an analyzing and controlling module, wherein the analyzing and controlling module performs an analyzing process for calculated a value of sensitivity S based on the electric signal, wherein the analyzing and controlling module can identify the specie(s) of the VOCs through comparing the calculated sensitivity value S with the sensitivity value S corresponding to a number of specific VOCs stored in a default database, wherein the analyzing and controlling module can generate a controlling signal to show what specie(s) the VOCs is, what concentration the VOC(s) is, and where the VOCs detected.

The mentioned light providing module comprises a first light source and a second light source, wherein when the detecting module exposed to an environment with VOCs, the light absorption peak of the first light source is unaffected and being as the control standard value, and the light absorption peak of the second light source is varied with the material change of the detecting module so that the light absorption peak of the second light source is as the detective variation value. The selection of the first light source and the second light source is from one of the following wavelength pair: the wavelength of the first light source at about 510 nm to 520 nm and the wavelength of the second light source at about 550 nm to 610 nm, the wavelength of the first light source at about 545 nm to 585 nm and the wavelength of the second light source at about 630 nm to 650 nm, the wavelength of the first light source at about 690 nm to 700 nm and the wavelength of the second light source at about 745 nm to 755 nm. The detecting module comprises a detecting layer, wherein the detecting layer is opposite to the light irradiating direction of the light providing module for receiving the light from the light providing module. The thickness of the detecting layer is about 10 nanometer to 10 micrometer. According to this invention, the detectable limitation of VOCs concentration of the detecting module is depended on controlling the thickness of the detecting layer of the detecting module. The detecting layer comprises a conductive polymer and an anti-π-π stacking compound, wherein the anti-π-π stacking compound is in nanoscale, wherein the conductive polymer is with the molecular structure of π-π stacking effect. The molecular weight of the conductive polymer is about 5 to 100 kDa (kilodaltons). The conductive polymer is selected from one of the following, the derivatives thereof, or any combinations thereof: poly(3-hexylthiophene) (P3HT), poly(p-phenylene vinylene), polyfluorene, poly(thieno[3,4-b]-thiophene-alt-benzodithiophene), poly(thiophene-alt-isoindigo), poly(cyclopentadithiophene-alt-isoindigo), poly(diketopyrrolopyrrole-alt-4,5-diaza-9,9'-spirobifluorene), {poly(cyclopentadithiophene-alt-benzothiadiazole)}, poly[2,6-(4,4-bis(2-ethylhexyl)-4H-cyclopenta[2,1-b;3,4-b']dithiophene)-alt-4,7(2,1,3-benzothizdiazle)] (PCPDTBT), and poly(benzodithiophene-thiophene-cyanovinylene) (PCBN). The anti-π-π stacking compound is selected from one of the following, the derivatives thereof, or any combinations thereof: inorganic nanomaterials, fullerene derivatives. The fullerene derivatives is selected from one of the following, the derivatives thereof, or any combinations thereof: (6,6)-phenyl-$C_{61}$ butyric acid methyl ester ($PC_{61}BM$), (6,6)-phenyl-$C_{71}$ butyric acid methyl ester ($PC_{71}BM$). The weight percentage of the fullerene derivatives and the conductive polymer is 1:5 to 5:1. The inorganic nanomaterials is selected from one of the following, the derivatives thereof, or any combinations thereof: copper sulfide, zinc sulfide, bismuth sulfide, cadmium selenide, zinc oxide, tungsten oxide, titanium oxide. The weight percentage of the inorganic nanomaterials in the total weight is about $1 \times 10^{-5}:1$ to $1 \times 10^{-3}:1$. The default database can provide the sensitivity S corresponding to the specific VOCs, wherein the sensitivity S can be determined as $S_a$ and $S_v$ with the voltage difference $\Delta V$ or absorbance A:

$$S_a = [(A_x/A_y)_a/(A_x/A_y)_b] - 1,$$

$$S_v = [(\Delta V_x/\Delta V_y)_a/(\Delta V_x/\Delta V_y)_b] - 1,$$

wherein x is represented the wavelength of the second light source, y is represented the wavelength of the first light source, a is represented the condition before exposed to VOCs, and b is represented the condition after exposed to VOCs. The mentioned method for detecting VOCs can further comprise a step of performing an alarming process by an alarming module to generate.

According to the above objectives, this present invention provides a device for detecting VOCs. The mentioned device for detecting VOCs comprises an outer case comprising a gas-introducing port and an accommodating space, wherein the gas-introducing port is used for introducing the air outside the outer case into the accommodating space; a reference light source and a detective light source, wherein the reference light source and said detecting light source are individually placed at a first specific location in the outer case, wherein the reference light source and the detective light source at the first specific locations are parallel each other, wherein the light absorption peak of the reference light source is unaffected and being as the control standard value, wherein the light absorption peak of the detective light source is varied while changing a detecting material and being as the detective variation value; a VOC detecting element located at a second specific location in the outer case, wherein the VOC detecting element is located in the direction of the optical path of the reference light source and the detecting light source for receiving the light from the reference light source and the detecting light source, wherein the accommodating space is between the first specific location and the second specific location, wherein the VOC detecting element comprises a conductive polymer and an anti-π-π stacking compound, wherein the anti-π-π stacking compound is in nanoscale, wherein the conductive polymer is with the molecular structure of π-π stacking effect; a light sensing element located on a third specific location at the outer case, wherein the third specific location is in the direction, as the same as the direction of the VOC detecting element, of the optical path of the reference light source and the detecting light source for detecting the absorbance variation of the light from the reference light source and the detecting light source and across the VOC detecting element, wherein the light sensing element can perform photo-electric conversion, wherein the light sensing element can convert the detected absorbance variation into voltaic variation and generate a voltaic signal; and an analyzing and controlling element comprising a default database, wherein the analyzing and controlling element compares the voltaic signal received from the light sensing element with the data in the default database to indentify whether there is any VOC in the gas in the accommodating space, wherein if there is VOC(s) in the accommodating space, the analyzing and controlling element will generate a controlling signal.

The reference light source and the detecting light source comprise a laser light source or a light emitting diode (LED) light source. The thickness of the VOC detecting element is about 50 nanometers to 120 nanometers. The conductive polymer is selected from one of the following, the derivatives thereof, or any combinations thereof: poly(3-hexylthiophene) (P3HT), poly(p-phenylene vinylene), polyfluorene, poly(thieno[3,4-b]-thiophene-alt-benzodithiophene), poly(thiophene-alt-isoindigo), poly(cyclopentadithiophene-alt-isoindigo), poly(diketopyrrolopyrrole-alt-4,5-diaza-9,9'-spirobifluorene), {poly(cyclopentadithiophene-alt-benzothiadiazole)}, poly[2,6-(4,4-bis(2-ethylhexyl)-4H-cyclopenta[2,1-b;3,4-b']dithiophene)-alt-4,7(2,1,3-benzothizdiazle)] (PCPDTBT), and poly(benzodithiophene-thiophene-cyanovinylene) (PCBN). The anti-π-π stacking compound is selected from one of the following, the derivatives thereof, or any combinations thereof: inorganic nanomaterials, fullerene derivatives. The fullerene derivatives is selected from one of the following, the derivatives thereof, or any combinations thereof: (6,6)-phenyl-$C_{61}$ butyric acid methyl ester ($PC_{61}BM$), (6,6)-phenyl-$C_{71}$ butyric acid methyl ester ($PC_{71}BM$). The weight percentage of the fullerene derivatives and the conductive polymer is 1:1. The inorganic nanoparticles is selected from one of the following, the derivatives thereof, or any combinations thereof: copper sulfide, zinc sulfide, bismuth sulfide, cadmium selenide, zinc oxide, tungsten oxide, titanium oxide. The weight percentage of the inorganic nanomaterials in the total weight is $3\times10^{-5}$. The default database can provide the sensitivity S corresponding to the specific VOCs, wherein the sensitivity S can be determined as Sa and Sv with the voltage difference $\Delta V$ or absorbance A:

$$S_a = [(A_x/A_y)_a/(A_x/A_y)_b] - 1,$$

$$S_v = [(\Delta V_x/\Delta V_y)_a/(\Delta V_x/\Delta V_y)_b] - 1,$$

wherein x is represented the wavelength of the second light source, y is represented the wavelength of the first light source, a is represented the condition before exposed to VOCs, and b is represented the condition after exposed to VOCs.

The light sensing element can be a solar apparatus. The mentioned device for detecting VOCs can further comprise an alarming element and a displaying element, wherein the alarming element and the displaying element are individually electric coupled with the analyzing and controlling element, wherein the controlling signal is respectively sent to the alarming element and the displaying element, wherein the displaying element shows the relative information of the detected VOCs based on the controlling signal, wherein the alarming element generates a light warning, a sound warning, or the combination thereof based on the controlling signal.

DETAILED DESCRIPTION OF THE PREFERRED EMBODIMENTS

The present invention is directed to a detecting system for volatile organic compounds and the method for forming the same and utility thereof. In order to facilitate understanding of the present invention, detailed structures and their elements and method steps are set forth in the following descriptions. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater details in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Figure 1:
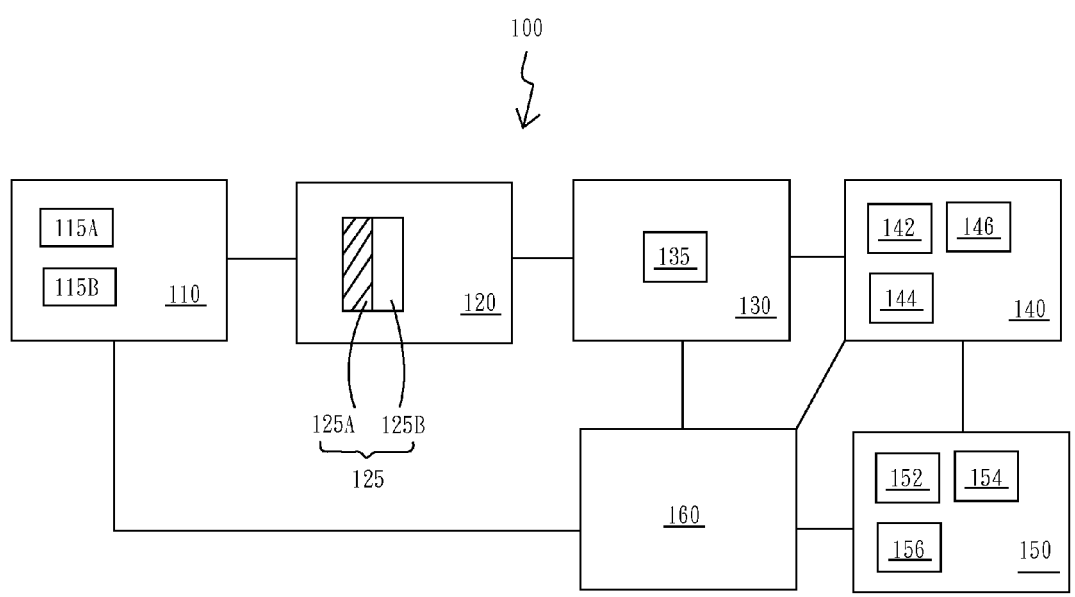
FIG. 1 shows a system for detecting VOCs according to a preferred embodiment of the present invention.

The first embodiment according to this specification discloses a detecting system for volatile organic compounds (VOCs) 100, as shown in FIG. 1. The detecting system for VOCs 100 comprising: a light providing module 110, a detecting module 120, a light sensing module 130, an analyzing and controlling module 140, an alarming module 150, and a power supplying module 160. The light providing module 110 is employed for providing full-spectrum light source. In one preferred example of this embodiment, the light providing module 110 can further comprise a laser light module, or a light emitting diode (LED) light source. The detecting module 120 is located at a first specific location in the optical path of the light providing module 110, so that the detecting module 120 can receive light energy from the light providing module 110. The mentioned detecting system for VOCs 100 can further comprises an accommodating part between the light providing module 110 and the detecting module 120 for introducing the VOC(s). In one preferred example of this embodiment, the detecting module 120 is displace-able. The light sensing module 130 is located at a second specific location in the optical path of the light providing module 110. The mentioned second specific location is in the direction, as the same as the direction of the first specific location, of the optical path of the light providing module 110, and the light sensing module 130 can detect the energy change of the light from the light providing module 110 and across the detecting module 120. The mentioned energy change of the light comprises the change of light intensity, and the degree of light absorption. The analyzing and controlling module 140 can communicate with the light sensing module optical 130, receive the signal of the energy change of the light of light sensing module 130, and determine whether there is VOC(s) in-situ by analyzing the above-mentioned signal from the light sensing module 130. The alarming module 150 can communicate the analyzing and controlling module 140, receive the controlling signal from the analyzing and controlling module 140, and release an alert to the surrounding. The power supplying module 160 is respectively electric coupled with all the above-mentioned modules, and can supply necessary power to those modules for keeping those modules working normally. The power supplying module 160 comprises a portable power supplying device, such as rechargeable battery (for example, lithium battery), the self-charging power supplying device (for example, solar cell), AC-DC power supplying device.

The light providing module 110 comprises a first light source 115A, and a second light source 115B. When the detecting module 120 is exposed to the environment of the VOCs, the light absorption peak of the first light source 115A is unaffected and can be used as the standard of control group. The light absorption peak of the second light source 115B will be changed with the material in the detecting module 120, and the light absorption peak of the second light source 115B can be used as the experimental data of the detection. In one preferred example of this embodiment, the first light source 115A and the second light source 115B are paired each other. When using different detecting material in the detecting system 100, different light source with different wavelength will be employed. For example, when using P3HT as the detecting material, the paired wavelength range of the light providing module 110 is: the wavelength range of the first light source 115A is about 510 nm to 520 nm, and the wavelength range of the second light source 115B is about 550 nm to 610 nm. When using PCBN as the detecting material, the paired wavelength range of the light providing module 110 is: the wavelength range of the first light source 115A is about 545 nm to 585 nm, and the wavelength range of the second light source 115B is about 630 nm to 650 nm. When using PCPDTBT as the detecting material, the paired wavelength range is: the wavelength range of the first light source 115A is about 690 nm to 700 nm, and the wavelength range of the second light source 115B is about 745 nm to 755 nm.

In one preferred example of this embodiment, the detecting module 120 can further comprise a light-transmissive detecting device 125. The light-transmissive detecting device 125 can be disposable, so that the detecting system 100 can be kept from the pollution of VOCs. Besides, the disposable light-transmissive detecting device 125 also can improve the detecting reliability of the detecting system 100, keep the light sensing module 130 from being directly contacted, and significantly extend the overall lifetime of the detecting system 100. The mentioned light-transmissive detecting device 125 can further comprise a detecting layer 125A, and a transparent substrate 125B. The detecting layer 125A is placed at the position opposite to the light providing module 110, and the detecting layer 125A can directly receive the light from the light providing module 110. The transparent substrate 125B can be an oxide glass substrate, a transparent plastic substrate, or other substrate with high light-transmissive property, such as ITO. The detecting layer 125A is formed onto one surface of the transparent substrate 125B by coating. In one preferred example, the thickness of the detecting layer 125A is approximately 10 nm to 10 um, preferably between from 50 nm to 150 nm. If the detecting layer 125A is not thick enough, the molecular morphology will not be changed by enough π-π stacking effect introduced while the conductive polymer contacting the VOCs. But, if the detecting layer 125A of the light-transmissive detecting device 125 is too thick, the transmittance and the sensitivity of the light-transmissive detecting device 125 will be decreased.

In one preferred example, the composition of the mentioned detecting layer 125A comprises a conductive polymer, and an anti-π-π stacking compound in nanoscale. The mentioned conductive polymer is with the molecular structure of the π-π stacking effect, and can be selected from one of the following, or the derivatives thereof, or any combinations thereof: poly(3-hexylthiophene) (P3HT), poly(p-phenylene vinylene), polyfluorene, poly(thieno[3,4-b]-thiophene-alt-benzodithiophene), poly(thiophene-alt-isoindigo), poly(cyclopentadithiophene-alt-isoindigo), poly(diketopyrrolopyrrole-alt-4,5-diaza-9,9'-spirobifluorene), {poly (cyclopentadithiophene-alt-benzothiadiazole)}, poly[2,6-(4, 4-bis(2-ethylhexyl)-4H-cyclopenta[2,1-b ;3,4-b'] dithiophene)-alt-4,7(2,1,3-benzothizdiazle)] (PCPDTBT), poly(benzodithiophene-thiophene-cyanovinylene) (PCBN). Preferably, the conductive polymer is selected from 3-hexylthiophene (P3HT), PCBN, PCPDTBT, the derivatives thereof, or any combinations thereof.

The above mentioned anti-π-π stacking compound in nanoscale can be nanoparticles or nanorods. The particle size of the anti-π-π stacking compound is suitable for entering the space inside the π-π stacking effect molecular structure of the conductive polymer to prevent the π-π stacking effect happening during forming the detecting layer 125A. The anti-π-π stacking compound in nanoscale comprises inorganic nanomaterials, and fullerene derivatives. The fullerene derivatives is selected from one of the following, or the derivatives thereof, or any combinations thereof: (6,6)-phenyl-$C_{61}$butyric acid methyl ester ($PC_{61}BM$), (6,6)-phenyl-$C_{71}$ butyric acid methyl ester ($PC_{71}BM$). Preferably, the fullerene derivatives is (6,6)-phenyl-$C_{61}$ butyric acid methyl ester ($PC_{61}BM$). In one preferred example, the fullerene derivatives in nanoscale is blended with the conductive polymer, and the fullerene derivatives in nanoscale can insert between the molecular structures of the conductive polymer to avoid the molecular morphology of the detecting layer 125A changed by the π-π stacking effect of the conducting polymer during forming the detecting layer 125A. Therefore, the molecular morphology of the detecting layer 125A will not be changed during forming the detecting layer 125A, and the molecular morphology of the detecting layer 125A will start to be changed when the detecting layer 125A is exposed to VOCs. The above-mentioned inorganic nanoparticles are selected from one of the following, or the derivatives thereof, or any combinations thereof: copper sulfide, zinc sulfide, bismuth sulfide, cadmium selenide, zinc oxide, tungsten oxide, titanium oxide, titanium oxide, etc. Preferably, the inorganic nanomaterial is copper sulfide. The weight percentage of the above fullerene derivatives and the conductive polymer is about 1:5 to 5:1. Preferably, the weight percentage of the above fullerene derivatives and the conductive polymer is about 1:1. The weight percentage of the inorganic nanomaterials to the total weight is about $1\times10^{-5}$:1 to $1\times10^{-3}$:1. Preferably, the weight percentage of the inorganic nanomaterials to the total weight is about $3\times10^{-5}$:1. There are three ways of blending the materials for forming the detecting layer 125A: blending the conductive polymer with the fullerene derivatives, blending the conductive polymer with the inorganic nanomaterials, and blending the conductive polymer blended with the fullerene derivatives and the inorganic nanomaterials. The addition of the inorganic nanomaterials can increase the surface area of the detecting layer 125A exposed to VOCs, and enhance the sensitivity of the detecting layer 125A. Hence, among the above three ways of blending the materials, the most preferable way is blending the conductive polymer with the fullerene derivatives and inorganic nanomaterials, the preferable way is blending the conductive polymer with the fullerene derivatives, and then is blending the conductive polymer with the inorganic nanomaterials.

The above-mentioned light sensing module 130 comprises a light intensity detecting device 135, wherein the light intensity detecting device 135 has the function of photoelectric conversion function, for example, a solar module. The light intensity detecting device 135 is used for receiving the light from the light providing module 110 and across the detecting module 120, and converting the light into an electric signal. In one preferred example, the electric signal can further comprise a potential signal. When the detecting module 120 exposed to an environment with non-volatile organic compounds, the structure of the conductive polymer of the detecting layer 125A will not be changed, and the light received by the light intensity detecting device 135 does not have any change. When the detecting module 120 exposed to an environment with volatile organic compounds, the molecular structure of conductive polymer of the detecting layer 125A and the anti-π-π stacking compounds in nanoscale are affected by the volatile organic compounds, and an aggregating effect among different species is induced. The mentioned aggregating effect will make the π-π stacking effect happening in the molecular structure of the conductive polymer, and the morphology of the conductive polymer will be changed rapidly. Then, the absorption of the light energy will be changed with the change of the morphology of the conductive polymer. Accordingly, the light energy received by the light intensity detecting device 135 will be changed, and the electric signal will also be changed. Moreover, the concentration of VOCs will also influence the mentioned aggregating effect. If the concentration of VOCs is very low, only those anti-π-π stacking compounds at the portion contacting with VOCs will be moved away from the molecular structure of the conducting polymer, and the variation of the light absorption will be low. Conversely, if the concentration of the VOCs is gradually increased, more anti-π-π stacking compounds will be moved away from the molecular structure of the conducting polymer, and the variation of the light absorption will be raised. Therefore, through controlling the formed thickness of the detecting layer 125A, it can further achieve the purpose for detecting the level of the concentrations.

The above-mentioned analyzing and controlling module 140 is used for receiving the electric signal, and producing a controlling signal after calculating and analyzing the mentioned electric signal. The analyzing and controlling module 140 comprises an analyzing unit 142, a controlling unit 144, and a displaying unit 146. The analyzing unit 142 comprises a default database, and a default detecting area. The default database can provide all corresponding sensitivity Sa or Sv of specific VOCs. The sensitivity S can be defined by the voltage difference $\Box V$ or absorbance A, for example:

$$S_a = [(A_x/A_y)_a/(A_x/A_y)_b] - 1,$$

$$S_v = [(\Delta V_x/\Delta V_y)_a/(\Delta V_x/\Delta V_y)_b] - 1,$$

wherein x represents the wavelength of the second light source, y represents the wavelength of the first light source, a represents the data before exposed to VOCs, b represents the data after exposed to VOCs.

The above analyzing unit 142 can calculate the sensitivity $S_a$ or $S_v$ based on the electric signal of the analyzing and controlling module 140 communicated from the light intensity detecting device 135, and comparatively analyze the calculated result with the default database. When the sensitivity of the Sa or Sv is conformed to the data range of some specific VOCs in the default database, the analyzing and controlling module 140 will ask the controlling unit 144 to generate a controlling signal, and communicate the controlling signal with the alarming module 150 to release a warning. Additionally, the above-mentioned displaying unit 146 will communicate with the controlling unit 144 and show what type(s) the VOCs are, how the concentration change of the VOCs are, and where the VOCs are detected. The above alarming module 150 comprises a warning light source 152, a warning sound device 154, and a warning communication device 156. The warning communication device 156 can be a wireless communicating system, an internet, etc. to notify the emergency disposal units or rescue units where and what the VOCs are.

Figure 2:
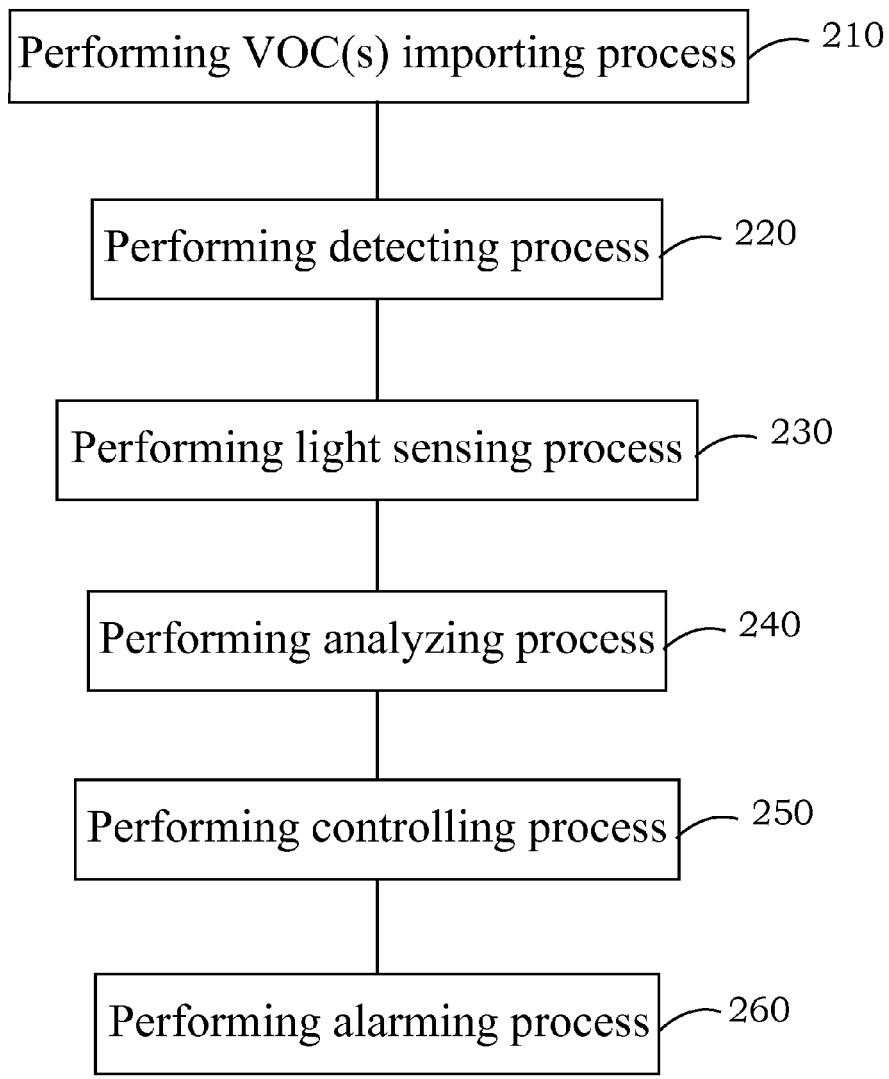
FIG. 2 shows a method for detecting VOCs according to a preferred embodiment of the present invention.

The second embodiment according to this specification discloses a detecting method for volatile organic compounds (VOCs), as shown in FIG. 2. In order to illustrate this embodiment more clearly, the following description also can be referred to FIG. 1. Firstly, the detecting system for VOCs 100 is provided. The inlet port of the detecting system for VOCs 100 is placed in a preset position, and a VOC importing process 210 is performed for importing the VOCs into an accommodating space of the detecting system for VOCs 100. Then, a detecting process 220 is performed by the detecting module 120, and the light-transmissive detecting device 125 of the detecting module 120 is employed to adequately contact with VOCs. The morphology of the conductive polymer of the detective layer 125A of the detecting module 120 will be rapidly changed with the π-π stacking effect of the molecular structure of the conductive polymer induced by the VOCs. Subsequently, a light sensing process 230 is performed by the light sensing module 130 for measuring the variation of absorbance (A), and a corresponding electric signal is generated. An analyzing process 240 is performed by the analyzing and controlling module 140. The analyzing unite 142 will process a calculation based on the electric signal to obtain the sensitivity $S_a$ or $S_v$. The analyzing and controlling module 140 will compare the calculated result with the sensitivity $S_a$ or $S_v$ data of specific VOCs in the default database of the analyzing unite 142, identify the specie(s) of the VOCs, and transfer the identified result to the controlling unite 144 of the analyzing and controlling module 140. A controlling process 250 is performed by the controlling unite 144 to generate a controlling signal, and the controlling unite 144 will respectively transfer the controlling signal to the displaying unite 146 and the alarming module 150. The displaying unite 146 will show the information of where and what the detected VOCs are. The alarming module 150 will perform an alarming process 260 according to the controlling signal to notify the emergency disposal unit or rescue units where took place. The notification from the alarming module 150 can comprise the type(s) of the detected VOCs, and the recently detected concentration of VOCs. The alarming process 260 can act as sound, light, and immediately communication through the light warning device 152, sound warning device 154, and communication warning device 156.

Figure 3:
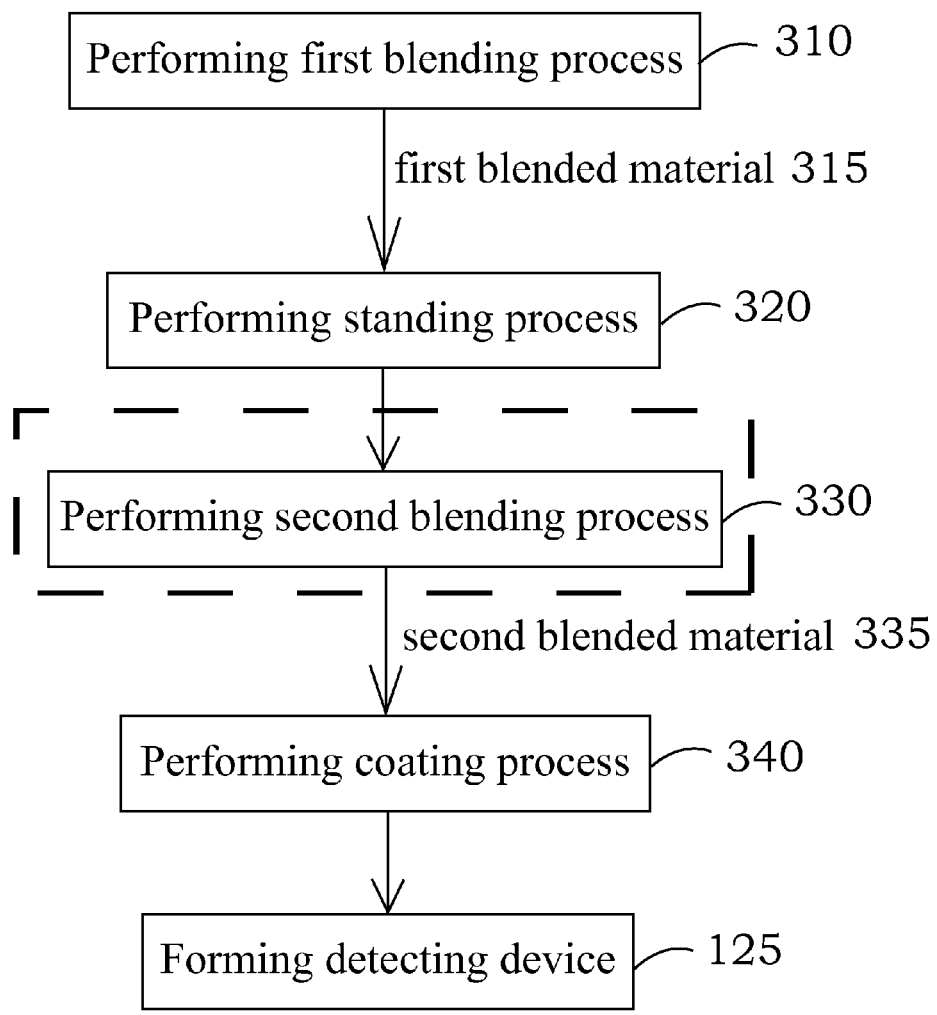
FIG. 3 shows a device for detecting VOCs and the method for forming it according to a preferred embodiment of the present invention.

The third embodiment according to this specification discloses a method for forming a detecting device for volatile organic compounds (VOCs), as shown in FIG. 3. Firstly, as the first blending process 310, a conductive polymer with π-π stacking effect molecular structure is blended with an anti π-π stacking compound in nanoscale in a solution to form a first blended material 315. The mentioned solution further comprises chlorobenzene. The conductive polymer and the anti-π-π stacking compound are respectively selected from the same groups as the foregoing embodiment about the materials and conditions of the detecting layer 125A. The blending weight ratio of the conductive polymer and the anti-π-π stacking compound is the same as the foregoing embodiments about the blending conditions of the detecting layer 125A. When employing the conductive polymer with higher molecular weight (Mw), the producing molecular structure will tend to be folded into a thin sheet-like structure. The molecular weight of the conductive polymer is higher; the detecting layer of the light-transmissive detecting device 125 with the conductive polymer is more sensitive. In one preferred example, the molecular weight of the conductive polymer can be about 5 to 100 kDa (kilodaltons). Subsequently, a standing process 320 is performed for the anti-π-π stacking compound inserting between the molecular structures of the conductive polymer and preventing the π-π stacking effect occurring during forming the detecting layer. Thereafter, it is optional to perform a second blending process 330 to add the inorganic nanomaterials into the first blended the material 315 to form a second blended material 335. In one preferred example, the inorganic nanomaterials can be selected from one of the following or the combination thereof: copper sulfide, zinc sulfide, bismuth sulfide, cadmium selenide, zinc oxide, tungsten oxide, titanium oxide. The inorganic nanomaterials is helpful on increasing the sensing area. The weight percentage proportion of the added inorganic nanomaterials to the overall weight is about $1 \times 10^{-5}:1$ to $1 \times 10^{-3}:1$, preferably about $3 \times 10^{-5}:1$.

Subsequently, a coating process 340 is performed to form the first blended material 315, or the second blend material 335, onto a transparent substrate and form the detecting layer. The technique for achieving the coating process 340 comprises: spin coating, spray coating, impregnation coating, and other technique known by the one skilled in the art. Preferably, the coating process 340 is accomplished by spin coating. Higher spin coating rate can form a thinner detecting layer, and the formed detecting layer can be dried rapidly. Higher spin coating rate also can keep the coating process 340 from producing more aggregated π-π stacked conductive polymer morphology. But, when the spin coating rate is too fast, the detecting layer will be formed too thin. A too thin detecting layer will cause that the π-π stacking effect cannot be triggered efficiently when the conductive polymer of the detecting layer contacting with the VOCs, and themorphology of the conductive polymer will not be changed. If the morphology of the conductive polymer of the detecting layer cannot be changed distinctly, the detected sensitivity S of the VOCs will be substantially decreased. On the other hand, when the detecting layer is formed by low spin coating rate, the thickness of the detecting layer will be formed too heavy, and the detected sensitivity S will be substantially decreased. In one preferred example of this embodiment, the thickness of the detecting layer is about 10 nm to 10 μm. Preferably, the thickness of the detecting layer is about 50 nm to 150 nm.

In one preferred example of this embodiment, the conductive polymer is poly(3-hexyl thiophene) (P3HT). The anti-π-π stacking compound is PCBM, the fullerene derivatives. The solvent is chlorobenzene. The temperature of the first blending process 310 is about 30 to 50° C. Preferably, the temperature of the first blending process 310 is about 40° C. The standing process 320 is performed for approximately 12-72 hours, preferably approximately 48 hours. The second blending process 330 is performed for about 2 to 5 hours, preferably about 3 hours. The coating process 340 is performed by spin-coating, and the spin coating rate is about 1000 to 10000 rpm, preferably about 5000 rpm.

Figure 4:
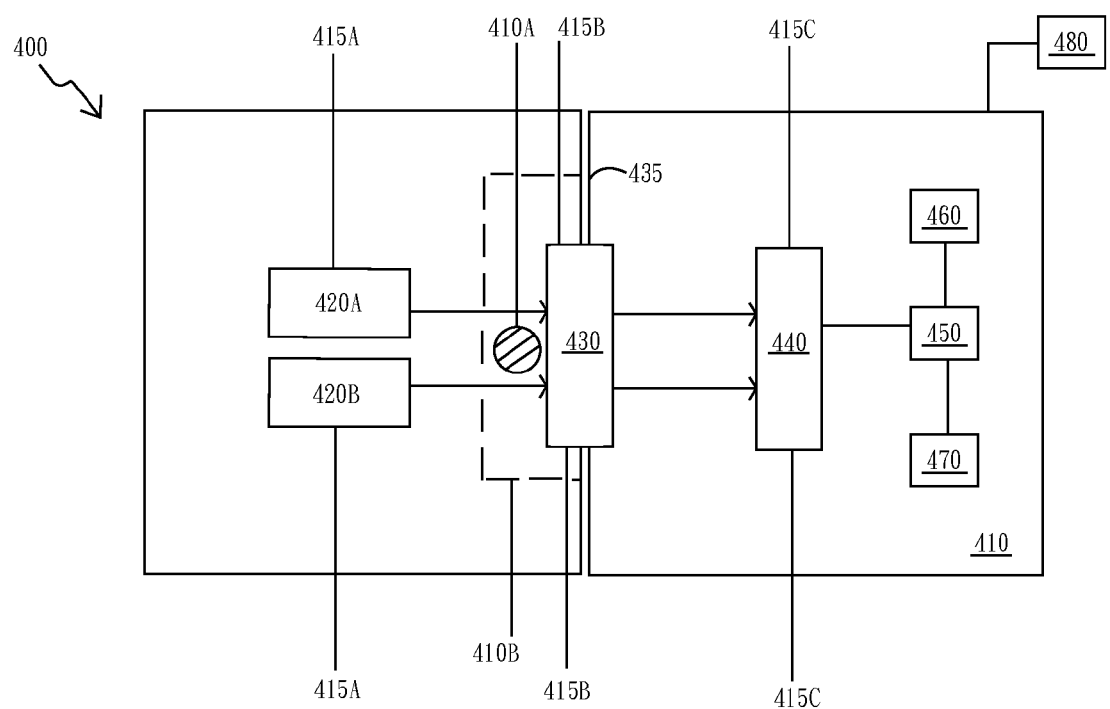
FIG. 4 show a device for detecting VOCs according to a preferred embodiment of the present invention.

The fourth embodiment according to this specification discloses a detecting device for volatile organic compounds (VOCs) 400, as shown in FIG. 4. The mentioned detecting device 400 comprises an outer case 410, a reference light source 420A, a detective light source 420B, a VOC detecting element 430, a plurality of supporting mechanism 435, a light sensing element 440, an analyzing and controlling element 450, an alarming element 460, a displaying element 470, and a power supplying element 480. The power supplying element 480 is employed for supplying sufficient power to the entire detecting device 400. The mentioned supporting mechanism 435 is used to support or clamp the components of the detecting device 400. The supporting mechanism 435 can be directly formed on the specific internal area of the outer case 410 or be made individually.

Referred to FIG. 4, mentioned outer case 410 comprises a gas-introducing port 410A, and an accommodating space 410B. The gas-introducing port 410A is employed for introducing the air outside the outer case 410 into the accommodating space 410B. The reference light source 420A and the detective light source 420B are individually placed at a first specific location 415A in the outer case 410. The reference light source 420A and the detective light source 420B at the first specific locations 415A are parallel each other. The reference light source 420A and the detective light source 420B can be selected from a laser light source or a light emitting diode light (LED) source. In one preferred example of this embodiment, the consideration about selecting the reference light source 420A and the detective light source 420B, such as the characteristics or the wavelength thereof, are as the same as the consideration of the light providing module 110 in the aforementioned embodiments.

The VOC detecting element 430 is located at a second specific location 415B in the outer case 410. The VOC detecting element 430 is located in the optical path of the reference light source 420A and the detective light source 420B, so that the VOC detecting element 430 can receive the light from the reference light source 420A and the detective light source 420B. The accommodating space 410B is between the first specific location 415A and the second specific location 415B. In one preferred example of this embodiment, the VOC detecting element 430 is displaceable. The above-described VOC detecting element 430 comprises a detecting layer, and a transparent substrate. The transparent substrate can be an oxide glass substrate, a transparent plastic substrate, or other substrate with high light-transmissive property, such as ITO. The mentioned detecting layer can be formed onto a surface of the transparent substrate by a coating process. The thickness of the detecting layer is approximately 10 nm to 10 um, preferably about 50 nm to 150 nm. In addition, the selection of the material of the mentioned detecting layer is as the same as the selection of the material of the detecting layer 125A described in the aforementioned embodiments.

The above light sensing element 440 is located at a third specific location 415C in the outer case 410. The third specific location 415C is positioned at the same direction of the light from the reference light source 420A and the detective light source 420B, so that the light sensing element 440 can detect the absorbance variation of the light from the reference light source 420A and the detective light source 420B and across the VOC detecting element 430. The light sensing element 440 can perform photo-electric conversion, and the received photo-variation can be converted into voltaic variation and generating a voltaic signal corresponding to the voltaic variation. In one preferred example, the light sensing element 440 is a solar apparatus. The mentioned analyzing and controlling element 450 can be electric coupled with the light sensing element 440, and the analyzing and controlling element 450 can receive the voltaic signal from the light sensing element 440. The analyzing and controlling element 450 will compare the received voltaic signal with a default database for analyzing whether the gas in the accommodating space 410B comprises VOC(s). According to the analyzing result, if the gas in the accommodating space 410B comprising VOC(s), the analyzing and controlling element 450 will generate a controlling signal. The alarming element 460 and the displaying element 470 are individually electric coupled with the analyzing and controlling element 450, and the alarming element 460 and the displaying element 470 can individually receive the controlling signal from the analyzing and controlling element 450. According to the received controlling signal, the displaying element 470 will show the relative information of the detected VOC(s), and the alarming element 460 will generate a light warning or a sound warning.

TABLE 1

| VOC | Sensitivity | Saturation Vapor Pressure (mmHg) | Solubility of P3HT (mg/ml) | Solubility of PCBM (mg/ml) |
|---|---|---|---|---|
| Water | 0.00 ± 0.02 | 24 | 0.0 | 0.0 |
| Methanol | 0.02 ± 0.05 | 125 | 0.0 | 0.0 |
| Ethanol | 0.02 ± 0.02 | 60 | 0.0 | 0.0 |
| 1-Propanol | 0.00 | 21 | 0.0 | 0.0 |
| n-Butanol | 0.00 | 6 | 0.0 | 0.0 |
| i-Pentane | 0.07 ± 0.02 | 532 | 0.0 | 0.0 |
| n-Hexane | 0.08 ± 0.03 | 151 | 0.1 | 0.1 |
| n-Octane | 0.17 | 14 | 0.1 | 0.1 |
| n-Decane | 0.12 | 1 | 0.2 | 0.1 |
| n-Dodecane | 0.04 | 0 | 0.2 | 0.1 |
| Toluene | 0.20 ± 0.02 | 28 | 0.4 | 2.8 |
| o-Xlene | 0.19 | 7 | 0.5 | 6.1 |
| m-Xylene | 0.17 | 8 | 0.5 | 5.8 |
| p-Xylene | 0.20 | 9 | 0.5 | 6.2 |
| Chlorobenzene | 0.20 ± 0.01 | 12 | 45 | 7.0 |
| Dichlorobenzene | 0.20 ± 0.02 | 1 | 37 | 27 |
| Chloroform | 0.28 ± 0.02 | 194 | 26 | 16 |
| Dichloromethane | 0.21 | 429 | 0.2 | 0.3 |
| 1,2-Dichloroethane | 0.13 | 79 | 0.0 | 2 |
| Tetrachloroethylene | 0.22 ± 0.03 | 18 | 33 | 1.2 |
| acetaldehyde | 0.15 ± 0.06 | 903 | 0.0 | 0.0 |
| Acetone | 0.07 | 231 | 0.0 | 0.1 |
| Diethyl ether | 0.15 ± 0.03 | 534 | 0.0 | 0.0 |

Figure 5:
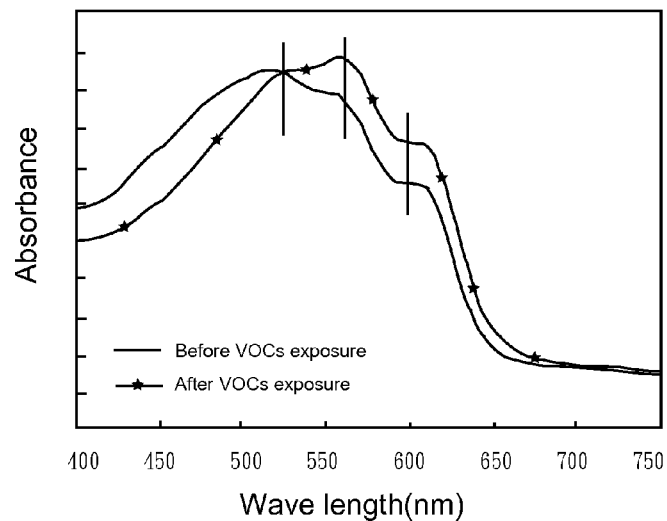
FIG. 5 shows absorption spectra of P3HT/PCBM film before and after exposed to chloroform vapor exposure according to the preferred embodiment of the present invention.
Figure 6:
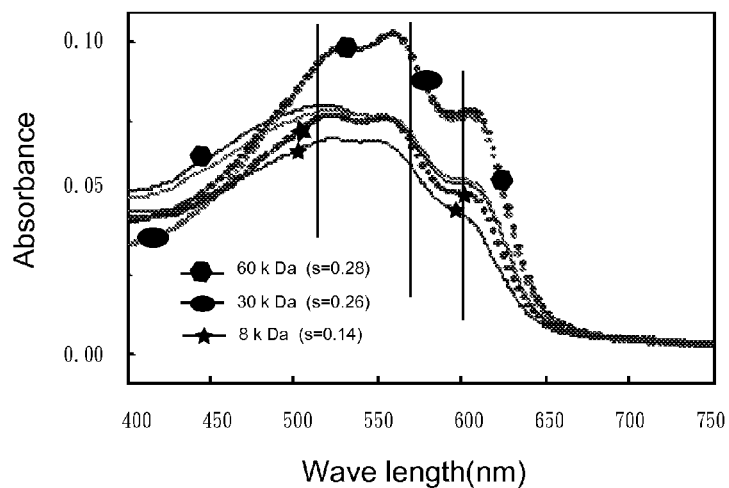
FIG. 6 shows absorption spectra of P3HT/PCBM film with different Mw of P3HT before (solid lines) and after (dotted lines) exposed to chloroform vapor exposure respectively according to the embodiment of the present invention.
Figure 7:
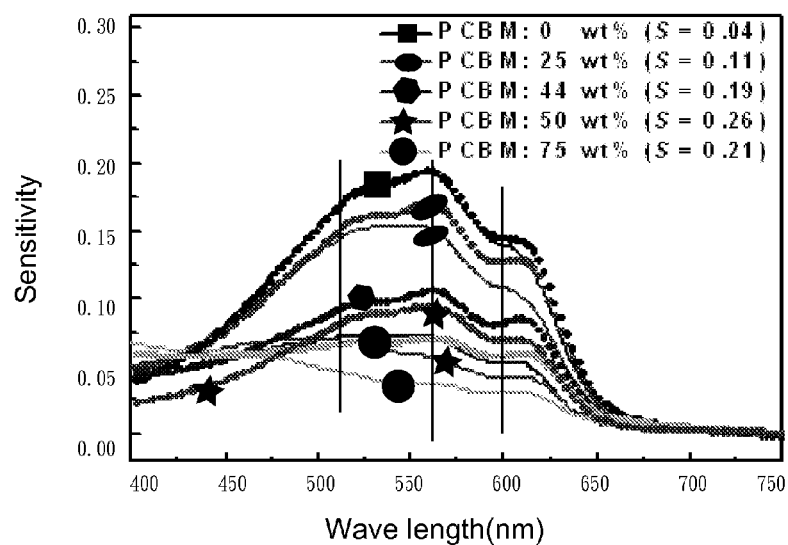
FIG. 7 shows absorption spectra of P3HT/PCBM film with different blending ratio before (solid lines) and after (dotted lines) exposed to chloroform vapor exposure respectively according to the preferred embodiment of the present invention.
Figure 8:
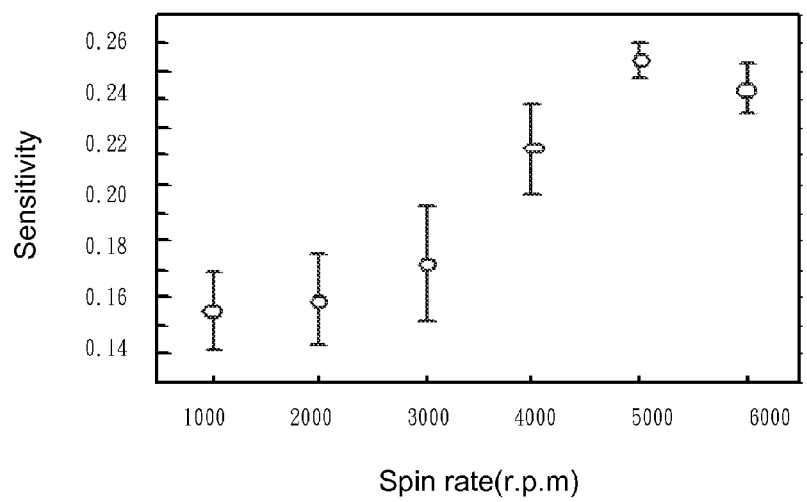
FIG. 8 shows the detected sensitivity of P3HT/PCBM films deposited from different spin rates according to the preferred embodiment of the present invention.

According to all the mentioned embodiments of the present invention, Table 1 presents an example of the corresponding data of some VOCs in the default database. In Table 1, it recites that the data of the sensitivity, the saturation vapor pressure of VOCs, and the solubility of P3HT and PCBM in different VOCs respectively. FIG. 5 illustrates the absorption spectra of P3HT/PCBM membrane before and after exposed to chloroform under saturation vapor pressure. Referred to FIG. 5, there are three specific absorbance peaks respectively marked at about 520 nm, 560 nm, and 610 nm. FIG. 6 presents the absorption spectra of P3HT and PCBM before (as the solid lines) and after (as the dotted lines) exposed to chloroform vapor. In FIG. 6, P3HT is with different molecular weight (Mw), as 8 kDa, 30 kDa, and 60 kDa. FIG. 7 presents the absorption spectra of P3HT and PCBM before (as the solid lines) and after (as the dotted lines) exposed to chloroform vapor, and the mixed ratio of P3HT in weight percentage is respectively 0%, 25% 50%, and 75%. FIG. 8 presents the sensitivity of P3HT/PCBM membrane deposited by different spin coating rates. Moreover, according to all embodiments of the present invention, when respectively blending different conductive polymer with PC61BM in the same proportion (weight percentage as 1:1) and exposing those to chloroform environment for two hours, the measured sensitivity respectively presents as: P3HT/PC61BM, $$S(A_{600nm}/A_{515nm})=1.26; PCPDTBT/PC_{61}BM,$$

$$S(A_{695nm}/A_{750nm})=1.12; PBCN/PC_{61}BM,$$

$$S(A_{640nm}/A_{580nm})=1.22$$

Every VOC has different characteristic sensitivity, and the simulating formula can be obtained from the sensitivity curve thereof. Based on those simulating formula, the database of VOCs can be established, and the database of VOCs can be used to help identifying the corresponding compound(s) in the following VOCs detecting applications. Therefore, the embodiments of the present invention can be applied to a variety of detecting materials. Moreover, the detecting device of the present invention does not react with water or alcohol, so that, when using the detecting device of this invention, the detecting signal will not be affected by water vapor without extra dehumidifying step for removing water.

The present invention provides a detecting device for detecting volatile organic compounds (VOCs) with high efficiency and low-cost. According to this present invention, conductive polymer blended with nano-particle is applied to detect a variety of VOCs through detecting the changes of the optical properties thereof. Under room temperature, the VOCs will cause softing effect to the detecting layer of this invention, and the morphology of the detecting layer will be changed rapidly. When the detecting materials contacting with the VOCs, the molecular structure and the morphology of the detecting materials of this invention will be changed by the VOCs, and the molecular structure of the detecting materials will be rearranged. The internal rearrangement of the detecting materials will directly present on the optical behavior of the detecting materials. Therefore, this invention can provide a VOCs detecting device/system with high sensitivity, high accuracy, speedy response, widely sensing range, and very low cost. Furthermore, the VOCs detecting system can be easily manufactured as a small size detector, such as a detective chip, and can be placed at any position with leaking danger of VOCs, such as pipeline junction or valve of tank. The VOCs detecting system of this invention can be installed at the pipeline junction and among the tank storaged VOCs so as to instantly monitor whether there is any VOCs leaked, and whether the VOCs concentration surrounding the tank is too high. The VOCs detecting system of this invention also can be installed in cars, elevators, cabin, factories, laboratories, or any space with the necessary of monitoring possible VOCs leakage. The detecting device/system can detect the vapor of low concentration VOCs to PPM level, and generate response immediately. So that, when VOCs leakage happening, the warning will be alarmed in few seconds to few minutes, and people can perform corresponding rescue instantly.

It is apparent that based on the above descriptions of the embodiments, the present invention can have numerous modifications and alterations, and they should be construed within the scope of the following claims. In addition to the above detailed descriptions, the present invention can be widely applied to other embodiments. The above embodiments are merely preferred embodiments of the present invention, and should not be used to limit the present invention in any way. Equivalent modifications or changes can be made by those with ordinary skill in the art without departing from the scope of the present invention as defined in the following appended claims.

What is claimed is:

1. A detecting material for detecting volatile organic compounds (VOCs), comprising:
   a conductive polymer with the molecular structure of π-π stacking effect; and
   an anti-π-π stacking compound in nanoscale, wherein the anti-π-π stacking compound in nanoscale is dispersed in the molecular structure of the conductive polymer to keep the morphology of the molecular structure of the conductive polymer away from being changed by π-π stacking effect;
   wherein the anti-π-π stacking compound will aggregate and move away from the molecular structure of the conductive polymer when the anti-π-π stacking compound contacting with VOC, wherein the morphology of the molecular structure of the conductive polymer will rapidly changed by π-π stacking effect when the anti-π-π stacking compound moving away from the molecular structure of the conductive polymer.

2. The detecting material for detecting VOCs of claim 1, wherein the conductive polymer is selected from one of the following, the derivatives thereof, or any combinations thereof: poly(3-hexylthiophene) (P3HT), poly(p-phenylene vinylene), polyfluorene, poly(thieno[3,4-b]-thiophene-alt-benzodithiophene), poly(thiophene-alt-isoindigo), poly(cyclopentadithiophene-alt-isoindigo), poly(diketopyrrolopyrrole-alt-4,5-diaza-9,9'-spirobifluorene), {poly(cyclopentadithiophene-alt-benzothiadiazole)}, poly[2,6-(4,4-bis(2-ethylhexyl)-4H-cyclopenta[2,1-b;3,4-b]dithiophene)-alt-4,7(2,1,3-benzothizdiazle)] (PCPDTBT), and poly(benzodithiophene-thiophene-cyanovinylene) (PCBN).

3. The detecting material for detecting VOCs of claim 1, wherein said anti-π-π stacking compound is selected from one of the following, or any combinations thereof: inorganic nanomaterials, fullerene derivatives.

4. The detecting material for detecting VOCs of claim 3, wherein said fullerene derivatives is selected from one of the following, the derivatives thereof, or any combinations thereof: (6,6)-phenyl-$C_{61}$ butyric acid methyl ester ($PC_{61}BM$), (6,6)-phenyl-$C_{71}$ butyric acid methyl ester ($PC_{71}BM$).

5. The detecting material for detecting VOCs of claim 3, wherein the weight percentage of the fullerene derivatives and the conductive polymer is 1:5 to 5:1.

6. The detecting material for detecting VOCs of claim 3, wherein the inorganic nanomaterials is selected from one of the following, the derivatives thereof, or any combinations thereof: copper sulfide, zinc sulfide, bismuth sulfide, cadmium selenide, zinc oxide, tungsten oxide, titanium oxide.

7. The detecting material for detecting VOCs of claim 1, wherein the weight percentage of the inorganic nanomaterials to the total weight is $1\times10^{-5}:1$ to $1\times0^{-3}:1$.

8. The detecting material for detecting VOCs of claim 1, wherein the molecular weight of the conductive polymer is 5 to 100 kDa (kilodaltons).

9. A system for detecting volatile organic compounds (VOCs), comprising:
   a light providing module for providing full-spectrum light source;
   a detecting module located at a first specific location in one optical path of the light providing module to receive the light from the light providing module;
   an accommodating space between the light providing module and the detecting module, wherein the accommodating space is employed for introducing and storing the VOC;
   a light sensing module located at a second specific location in the same optical path of the light providing module to detect the light variation of the light from the light providing module and across the detecting module, wherein the light sensing module will generate a electric signal based on the light variation; and
   an analyzing and controlling module communicating with the light sensing module and receiving the electric signal from the light sensing module, wherein the analyzing and controlling module analyzes the electric signal to identify whether there is VOCs in-situ.

10. A system for detecting VOCs of claim 9, wherein said light providing module comprises a laser light source or a light emitting diode light source (LED).

11. A system for detecting VOCs of claim 9, wherein said light providing module comprises a first light source and a second light source, when said detecting module is exposed to the environment with VOCs, the light absorption peak of the first light source is unaffected and being as the control standard value, and the light absorption peak of said second light source is variated with the change the detecting material of the detecting module so that the light absorption peak of the second light source is as the detective variation value.

12. A system for detecting VOCs of claim 11, wherein the selection of the first light source and the second light source is from one of the following wavelength pair: the wavelength of the first light source at about 510 nm to 520 nm and the wavelength of the second light source about at 550 nm to 610 nm, the wavelength of the first light source at about 545 nm to 585 nm and the wavelength of the second light source at about 630 nm to 650 nm, the wavelength of the first light source at about 690 nm to 700 nm and the wavelength of the second light source at about 745 nm to 755 nm.

13. A system for detecting VOCs of claim 9, wherein said detecting module comprises a detecting layer, wherein the detecting layer is opposite to the light irradiating direction of the light providing module for receiving the light from the light providing module.

14. A system for detecting VOCs of claim 13, wherein the thickness range of the detecting layer is about 10 nanometer to 10 micrometer.

15. A system for detecting VOCs of claim 13, wherein the detectable limitation of the VOCs concentration is depended on controlling the thickness of the detecting layer of the system for detecting VOCs.

16. A system for detecting VOCs of claim 13, wherein the detecting layer comprises a conductive polymer, and an anti-π-π stacking compound, wherein the anti-π-π stacking compound is in nanoscale, wherein the conductive polymer is with the molecular structure of π-π stacking effect, wherein the anti-π-π stacking compound is dispersed into the molecular structure of the conductive polymer to prevent π-π stacking effect occurred in the conductive polymer, wherein the anti-π-π stacking compound will aggregate and move away from the molecular structure of the conductive polymer when the anti-π-π stacking compound contacting with VOC, wherein the morphology of the molecular structure of the conductive polymer will rapidly changed by π-π stacking effect when the anti-π-π stacking compound moving away from the molecular structure of the conductive polymer.

17. A system for detecting VOCs of claim 16, wherein the molecular weight of the conductive polymer is about 5 to 100 kDa (kilodaltons).

18. A system for detecting VOCs of claim 16, wherein the conductive polymer is selected from one of the following, the derivatives thereof, or any combinations thereof: poly(3-hexylthiophene) (P3HT), poly(p-phenylene vinylene), polyfluorene, poly(thieno[3,4-b]-thiophene-alt-benzodithiophene), poly(thiophene-alt-isoindigo), poly(cyclopentadithiophene-alt-isoindigo), poly(diketopyrrolopyrrole-alt-4,5-diaza-9,9'-spirobifluorene), {poly(cyclopentadithiophene-alt-benzothiadiazole)}, poly[2,6-(4,4-bis(2-ethylhexyl)-4H-cyclopenta[2,1-b;3,4-b']dithiophene)-alt-4,7(2,1,3-benzothizdiazle)] (PCPDTBT), poly(benzodithiophene-thiophene-cyanovinylene) (PCBN).

19. A system for detecting VOCs of claim 16, wherein the anti-π-π stacking compound is selected from one of the following, the derivatives thereof, or any combinations thereof: inorganic nanomaterials, fullerene derivatives.

20. A system for detecting VOCs of claim 19, wherein the fullerene derivatives is selected from one of the following, the derivatives thereof, or any combinations thereof: (6,6)-phenyl-$C_{61}$ butyric acid methyl ester ($PC_{61}BM$), (6,6)-phenyl-$C_{71}$ butyric acid methyl ester ($PC_{71}BM$).

21. A system for detecting VOCs of claim 19, wherein the weight percentage of the fullerene derivatives and the conductive polymer is 1:5 to 5:1.

22. A system for detecting VOCs of claim 19, wherein the inorganic nanomaterials are selected from one of the following, the derivatives thereof, or any combinations thereof: copper sulfide, zinc sulfide, bismuth sulfide, cadmium selenide, zinc oxide, tungsten oxide, titanium oxide.

23. A system for detecting VOCs of claim 22, wherein the weight percentage of the inorganic nanomaterials and the total weight is $1\times10^{-5}:1$ to $1\times10^{-3}:1$.

24. A system for detecting VOCs of claim 19, wherein the conducting layer is formed by one of the following way: blending the conductive polymer with the fullerene derivatives, blending the conductive polymer with the inorganic nanoparticles, and blending the conductive polymer with the fullerene derivatives and the inorganic nanoparticles.

25. A system for detecting VOCs of claim 9, wherein the light sensing module comprises a light intensity detecting device, wherein the light sensing module can perform photoelectric conversion by the light intensity detecting device, wherein the light intensity detecting device can receive the light from the light providing module and across the detecting module, and convert the received light into the electric signal.

26. A system for detecting VOCs of claim 9, wherein the analyzing and controlling module further comprises:
   an analyzing unit comprising a default database and a default detecting area, wherein the analyzing unit can analyze and calculate the electric signal to obtain the sensitivity S, wherein the sensitivity S is compared with the data in the default database; and
   a controlling unit, wherein when the sensitivity S is matched with a value range of VOC in the default database, the analyzing and controlling module will drive the controlling unit to generate a controlling signal.

27. A system for detecting VOCs of claim 26, wherein the analyzing and controlling module further comprises a displaying unit communicating with the controlling unit wherein the displaying unit can receive the controlling signal from the controlling unit and display the information of the specie(s) of the detected VOC(s), the concentration of the detected VOC(s), and the area where the VOC(s) is detected.

28. A system for detecting VOCs of claim 26, wherein the default database can provide the sensitivity S corresponding to the specific VOCs, wherein the sensitivity S can be determined as $S_a$ and $S_v$ with the voltage difference $\Delta V$ or absorbance A:

$$S_a = [(A_x/A_y)_a/(A_x/A_y)_b] - 1,$$

$$S_v = [(\Delta V_x/\Delta V_y)_a/(\Delta V_x/\Delta V_y)_b] - 1,$$

wherein x is represented the wavelength of the second light source, y is represented the wavelength of the first light source, a is represented the condition before exposed to VOCs, and b is represented the condition after exposed to VOCs.

29. A system for detecting VOCs of claim 9, wherein the analyzing and controlling module further comprises an alarming module, wherein the alarming module can receive the controlling signal and generate a warning, wherein the alarming module comprises a warning light device, a warning sound device, and a warning communicating device, wherein the warning communicating device can notify the emergency disposal units or the rescue units where the VOC(s) is, what specie(s) the VOC(s) is, and what concentration the VOC(s) is through wire or wireless communication.

* * * * *